(12) United States Patent
Rovaniemi

(10) Patent No.: US 10,687,984 B2
(45) Date of Patent: Jun. 23, 2020

(54) WOUND DRESSING WITH A SENSOR

(71) Applicant: Absorbest AB, Kisa (SE)

(72) Inventor: Rolf Rovaniemi, Rimforsa (SE)

(73) Assignee: ABSORBEST AB, Kisa (SE)

( * ) Notice: Subject to any disclaimer, the term of this patent is extended or adjusted under 35 U.S.C. 154(b) by 394 days.

(21) Appl. No.: 14/968,007

(22) Filed: Dec. 14, 2015

(65) Prior Publication Data

US 2016/0166438 A1 Jun. 16, 2016

(30) Foreign Application Priority Data

Dec. 16, 2014 (EP) .................................... 14198215

(51) Int. Cl.
| | | |
|---|---|---|
| *A61F 13/00* | (2006.01) | |
| *A61B 5/00* | (2006.01) | |
| *A61F 13/42* | (2006.01) | |

(52) U.S. Cl.
CPC .......... *A61F 13/00059* (2013.01); *A61B 5/00* (2013.01); *A61B 5/445* (2013.01); *A61F 13/00029* (2013.01); *A61F 13/00055* (2013.01); *A61F 13/00987* (2013.01); *A61F 13/42* (2013.01); *A61F 2013/422* (2013.01); *A61F 2013/424* (2013.01); *A61F 2013/426* (2013.01)

(58) Field of Classification Search
CPC ................ A61F 13/15; A61F 13/00055; A61F 13/00059; A61F 13/00029; A61F 13/00987; A61F 13/42; A61F 2013/4242; A61B 5/00; A61B 5/445
See application file for complete search history.

(56) References Cited

U.S. PATENT DOCUMENTS

| | | | |
|---|---|---|---|
| 2003/0078553 A1* | 4/2003 | Wada | A61F 13/42 604/361 |
| 2005/0137542 A1 | 6/2005 | Underhill et al. | |
| 2006/0129216 A1* | 6/2006 | Hastings | A61B 5/0215 607/115 |
| 2007/0024457 A1* | 2/2007 | Long | A61F 13/42 340/605 |
| 2008/0266117 A1* | 10/2008 | Song | A61F 13/42 340/573.5 |
| 2009/0209896 A1 | 8/2009 | Selevan | |
| 2013/0041334 A1* | 2/2013 | Prioleau | A61F 13/42 604/361 |
| 2013/0274629 A1 | 10/2013 | Duesterhoft et al. | |
| 2015/0018792 A1* | 1/2015 | Marsiquet | A61F 13/0246 604/361 |

FOREIGN PATENT DOCUMENTS

| | | |
|---|---|---|
| CA | 2583034 A1 | 9/2007 |
| DE | 102012211015 A1 | 2/2014 |

(Continued)

OTHER PUBLICATIONS

EP Patent Appln. No. 14198215.7, Extended Search Report, dated Jun. 26, 2015, 7 pg.

*Primary Examiner* — Paula J Stice

(74) *Attorney, Agent, or Firm* — Cuenot, Forsythe & Kim, LLC

(57) ABSTRACT

A wound dressing includes at least one sensor generating a sensor signal. The wound dressing also includes a display configured to receive the sensor signal from the at least one sensor and present data corresponding to the sensor signal.

21 Claims, 8 Drawing Sheets

(56) References Cited

FOREIGN PATENT DOCUMENTS

| EP | 3034054 A1 | 6/2016 |
|----|------------|--------|
| WO | 0150996 A1 | 7/2001 |
| WO | 2006103422 A1 | 10/2006 |
| WO | 2012012286 A1 | 1/2012 |
| WO | 2013026999 A1 | 2/2013 |
| WO | 2013114273 A1 | 8/2013 |

* cited by examiner

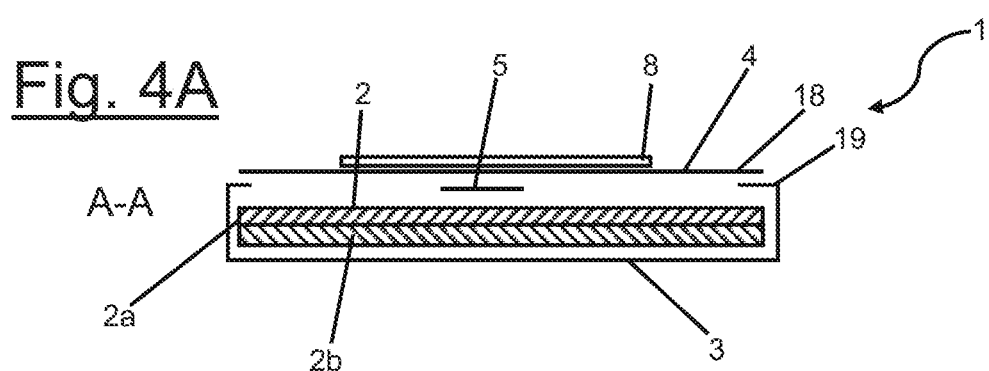
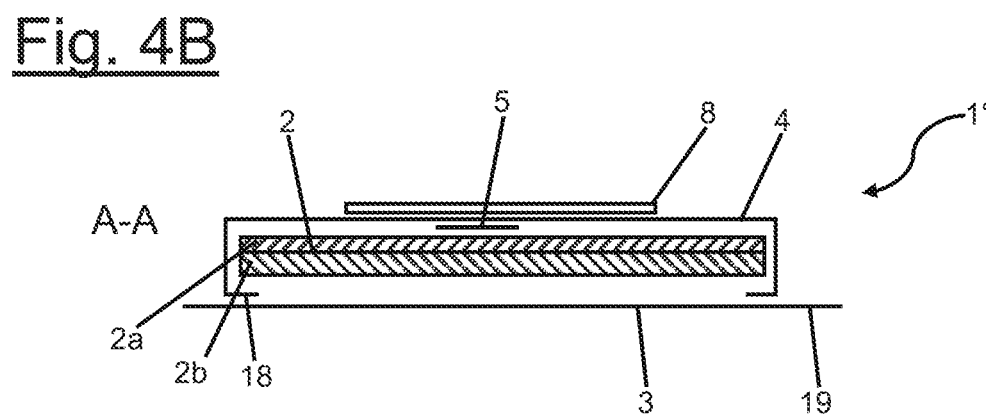
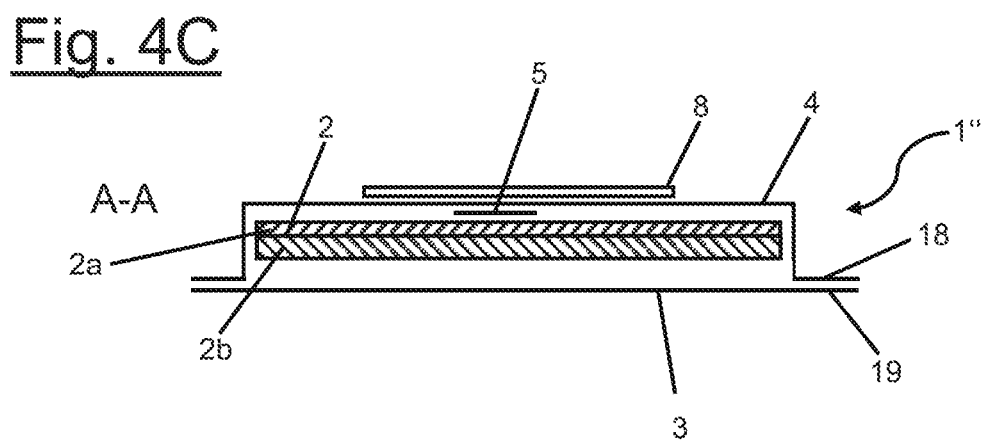
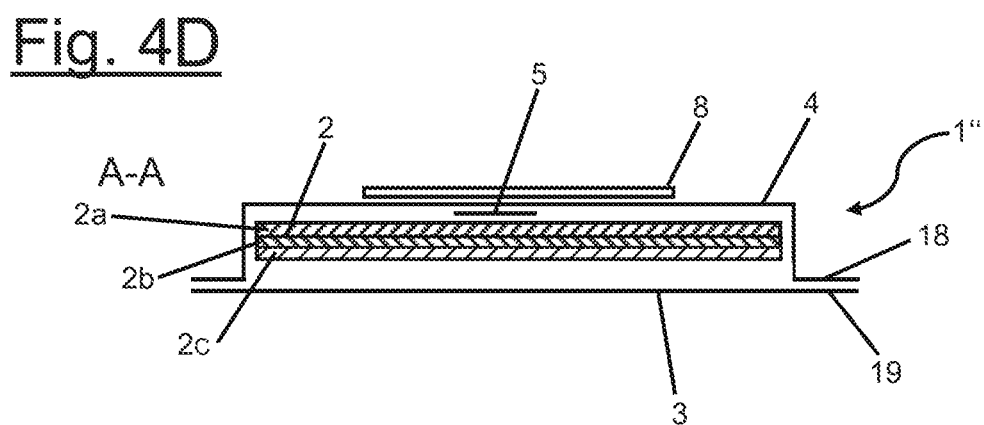

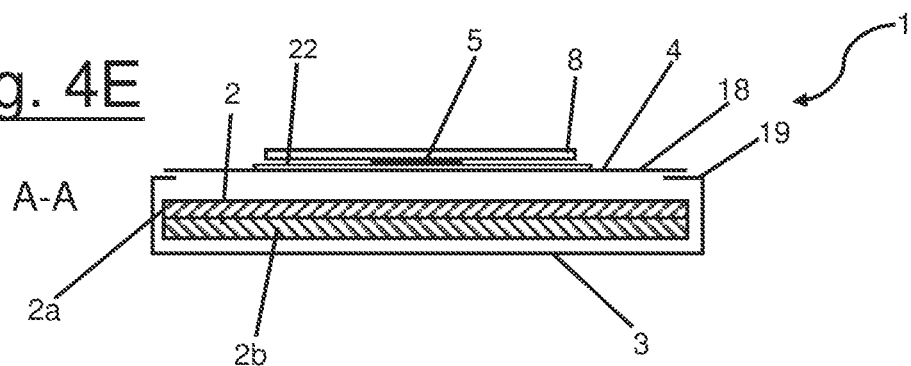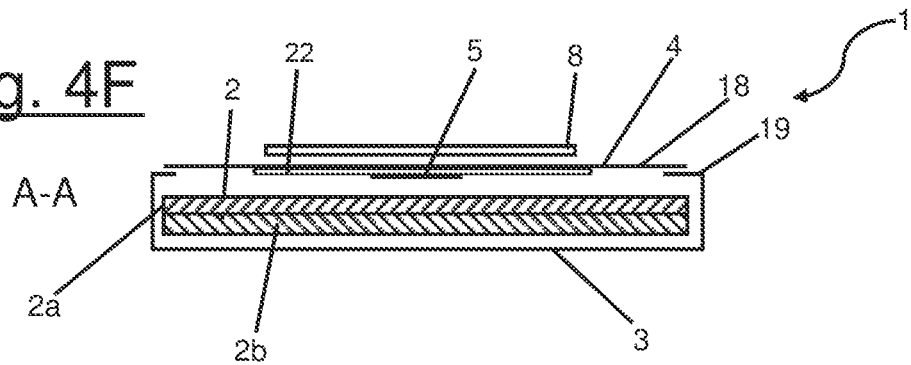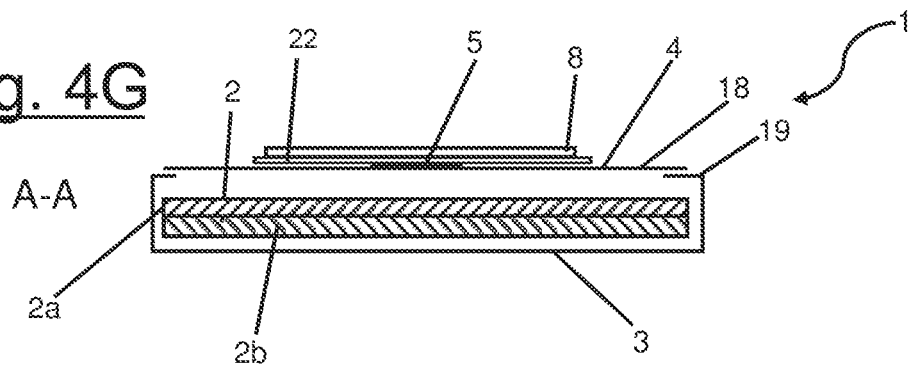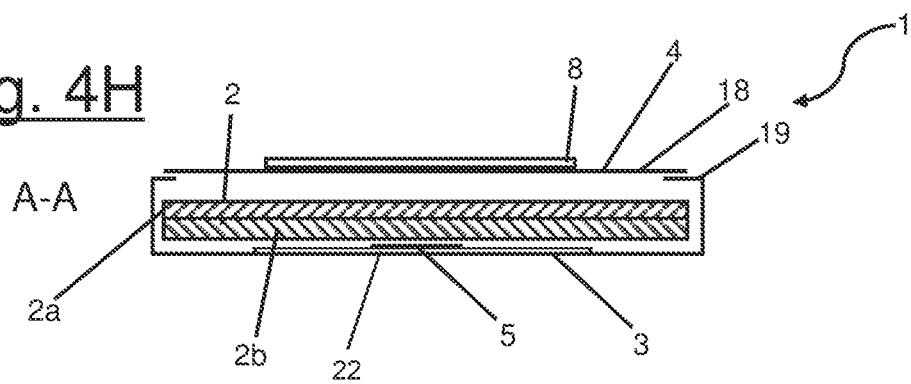

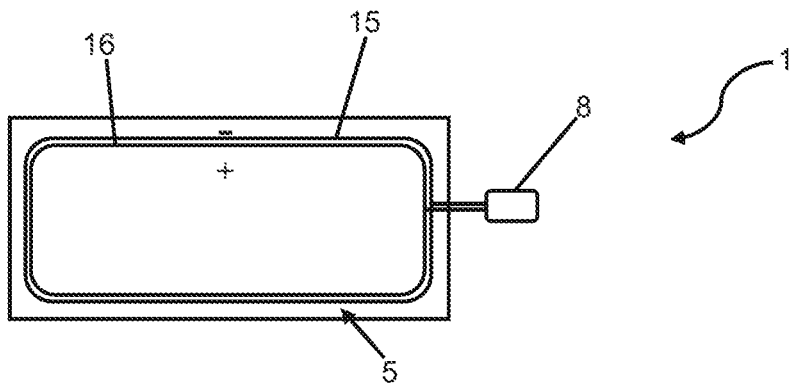
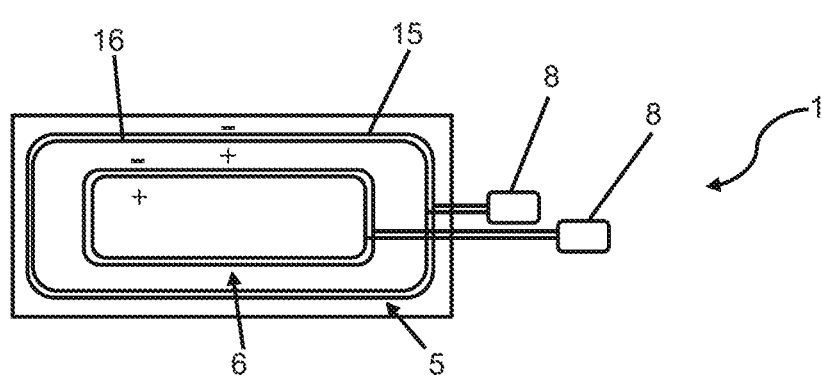
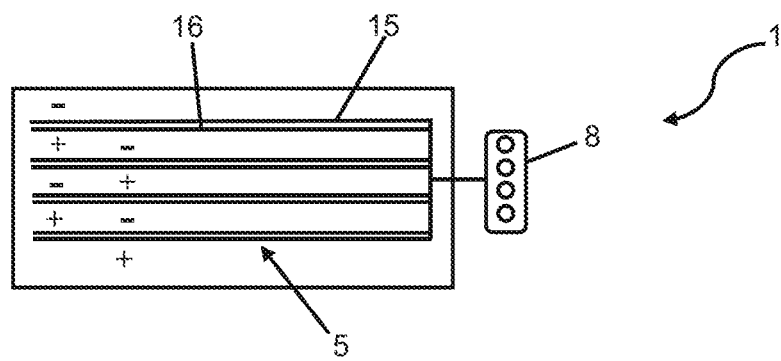
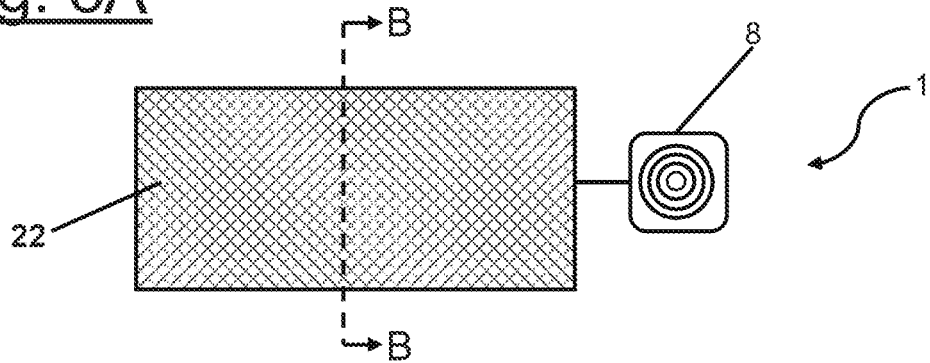

WOUND DRESSING WITH A SENSOR

CROSS-REFERENCE TO RELATED APPLICATIONS

This application claims the benefit of European Application Number 14198215.7 filed on Dec. 16, 2014, which is fully incorporated herein by reference.

STATEMENT REGARDING FEDERALLY SPONSORED RESEARCH OR DEVELOPMENT (Not Applicable)

The NAMES OF THE PARTIES TO A JOINT RESEARCH AGREEMENT (Not Applicable)

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

(Not Applicable)

STATEMENT REGARDING PRIOR DISCLOSURES BY THE INVENTOR OR A JOINT INVENTOR (Not Applicable)

BACKGROUND OF THE INVENTION

The present invention relates to wound dressings.

Wound dressings for covering wounds are known in various forms from the prior art. When applied to a wound, the dressings cover the wound such that the wound is prevented from being further harmed and may heal under the dressing.

In WO 2012/012286 A1, systems and methods are provided for sensing fluid in a dressing on a patient and producing an electrical signal. In one instance, a galvanic cell is used as an electronic detection device. The galvanic cell is placed in the dressing and produces a voltage when the dressing is substantially saturated.

WO 2013/114273 A1 relates to a wound dressing comprising an application surface for application to a wound, an absorbent structure for absorbing exudate discharged from the wound, an intermediate structure located between the application surface and the absorbent structure and arranged to promote distribution of exudate from the application surface to one or a plurality of inlet zones having a limited area in the absorbent structure, and a detection system to detect the extent of the absorbent structure that is wetted by the exudate having penetrated into the absorbent core via the inlet zone or zones.

In US 2013/0274629 A1, appurtenances to wound dressings are described, which include: a substrate configured to mechanically or chemically attach to a wound dressing, a transmission unit attached to a surface of the substrate, the transmission unit including circuitry and at least one antenna, the transmission unit configured to transmit a signal, and a projection operably attached to the transmission unit, the projection being of a size and shape to extend into an interior region of the wound dressing and configured to sample a fluid associated with a wound.

BRIEF SUMMARY OF THE INVENTION

A wound dressing includes at least one sensor generating a sensor signal. The wound dressing also includes a display configured to receive the sensor signal from the at least one sensor and present data corresponding to the sensor signal.

A method of manufacturing a wound dressing includes printing, onto the wound dressing, a display, the display configured to receive at least one sensor signal generated by at least one sensor and the display configured to present data corresponding to the sensor signal. The method also includes mounting to, or integrating with, the wound dressing the at least one sensor.

BRIEF DESCRIPTION OF THE SEVERAL VIEWS OF THE DRAWINGS

FIGS. 4A to 4H show schematic cross-sectional views along line A-A of FIG. 2 with different designs of the pouch formed by the backing and facing layers.

FIG. 5 shows a schematic drawing of a first sensor arrangement with a single sensor in the form of a closed loop.

FIG. 6 shows a schematic drawing of a second sensor arrangement comprising two sensors the form of a closed loops.

FIG. 7 shows a schematic drawing of a third sensor arrangement comprising four strip-shaped sensors.

FIG. 8A shows a schematic drawing of a fourth sensor arrangement with a net structure.

DETAILED DESCRIPTION OF THE INVENTION

Figure 1:
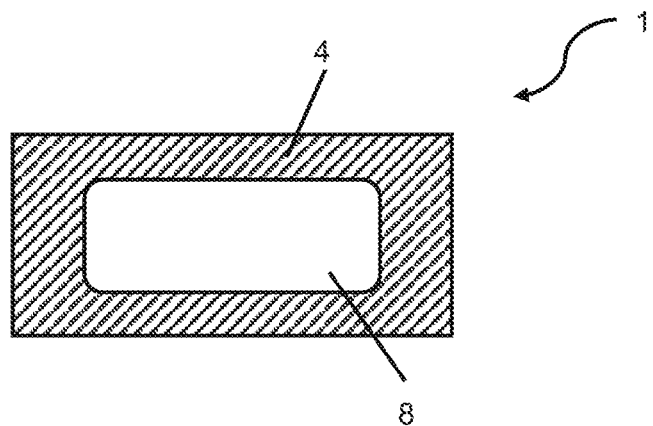
FIG. 1 shows a schematic top view onto the backing side of a wound dressing with a display according to a first embodiment of the present invention.

This disclosure relates to wound dressings.

Once a dressing is applied onto a wound, information on the status neither of the dressing nor of the healing are on hand, but have to be estimated based on experience. However, this has proven to be disadvantageous, especially in cases wherein unforeseen complications occur. When compared to the prior art it is an object of the present invention to provide an improved wound dressing, which is capable to provide status information on the wound dressing and/or on the wound in an easy and direct way of handling.

The above object is solved by a wound dressing, which comprises at least one sensor and a display, which is adapted to receive data determined by the sensor in form of an electrical signal and to display (i.e., present) the received data.

With a wound dressing according to the present invention status information on the wound dressing and/or on the wound are displayed (i.e., presented) in a direct and easy way on the display. Thus, the need for indicators is satisfied that provide corresponding status information after the dressing is applied to the wound.

A wound dressing in terms of the present application refers to any wound care article for covering a wound such that the wound is prevented from being further harmed and may heal under the dressing. A wound dressing may e.g. be a sterile pad, a compress, a bandage, an adhesive bandage, like a Band-Aid®, or a plaster.

In one embodiment the wound dressing comprises a backing layer. When the wound dressing is applied to a wound, the backing layer in one embodiment serves as a cover of the wound dressing, which is not in direct contact with the wound.

In an embodiment, the wound dressing is designed to be in direct contact with the wound. In one embodiment, according to the present invention, the wound dressing is adapted for absorbing wound exudate discharged from a wound.

In an embodiment according to the present invention, the wound dressing is an adhesive bandage comprising a backing layer, an absorbent pad and an adhesive film. In this embodiment the wound dressing is self-adhesive. In an embodiment, the absorbent pad is located (e.g., positioned) under the backing layer, wherein the absorbent pad is intended to come in direct contact with a wound and suitable to absorb blood from the wound. The backing layer prevents direct contact between the absorbent pad and e.g. a patient's clothing. For example a self-adhesive film may be applied to the bottom side of the backing layer or as a backing layer, which laterally extends beyond the absorbent pad. Those sections extending beyond the absorbent pad may be attached to a patient's skin. In a particular embodiment the wound dressing forms a plaster.

In one embodiment, the wound dressing comprises an absorbent core, a facing layer, and a backing layer, wherein the absorbent core is located (e.g., positioned) between the facing layer and the backing layer.

In the following placed/located on the backing layer refers to being placed/located on an exterior surface of the backing layer, i.e. on an exterior surface of the wound dressing. Placed/located under the backing layer refers to being placed/located on an interior surface of the backing layer, i.e. inside the wound dressing. Placed/located on the facing layer refers to being placed/located on an interior surface of the backing layer, i.e. the wound dressing. Placed/located under the facing layer refers to being placed/located on an exterior surface of the backing layer, i.e. the wound dressing, intended to make direct contact with the wound.

Wound fluid discharged from the wound bed is absorbed by the absorbent core of the dressing through the facing layer. Once the core is saturated, the dressing has to be replaced by a new one. Furthermore, when becoming saturated the dressing may tend to provide leakage of wound fluid. A problematic behavior of the absorbent core, particularly of those comprising a superabsorbent, is that the superabsorbent can create a "gel blocking" resulting in blocking of the lateral flow, which negatively influences the filling behavior of the absorbent core.

By a wound dressing according to the present invention indication may be provided in time before saturation or leakage of a wound dressing occur. In addition, a high local moisture content, which can be disadvantageous for a wound's healing process, may be determined based on the data provided by the display. Thus, it may be easily judged on basis of suitable indicators, when it is time to replace a wound dressing. In particular, even unforeseen complications like "gel blocking" may be resolved in time by replacing the wound dressing.

Wound dressings are in general intended as disposable items for reasons of hygiene. The wound dressing comprises a layered structure comprising at least a facing layer, an absorbent core and a backing layer. A wide range of suitable structures and materials may be used for the wound dressing.

In an embodiment, the absorbent core may be any structure suitable to absorb exudate from a wound. The material of the absorbent core in an embodiment may comprise any one of a group consisting of cellulose, regenerated cellulose, in particular cellulose fluff or regenerated cellulose fluff, air-laid cellulose or air-laid regenerated cellulose, tissue paper, a non-woven, a textile fabric, a foam, an alginate, ALT, and a hydrocolloid or a combination thereof. In one embodiment, the absorbent core is produced as a spunlaced web material of 100% pure cellulose or 100% regenerated cellulose. In another embodiment the absorbent core comprises a mixture of pure cellulose or regenerated cellulose and synthetic fibers. In yet another embodiment the absorbent core comprises a non-woven tamponade or pad containing sodium carboxymethyl cellulose and regenerated cellulose, as it is commercially available under the trade name Aquacel® from ConvaTec (Germany) GmbH of Munich, Germany.

In one embodiment of the present invention, the wound dressing comprises an absorbent pad, which is suitable to absorb blood from a wound. The material of the absorbent pad in an embodiment may comprise any one and any combination of the materials listed above as materials of an absorbent core.

In an embodiment of the invention, such a structure of the absorbent core may be used as a carrier layer to accommodate or carry an absorbent substance, in particular a superabsorbent substance.

The absorbent core of the wound dressing in an embodiment may be any structure comprising a superabsorbent substance. Superabsorbent substances in the sense of the present application are materials being able to absorb and retain large volumes of water in aqueous solutions. Superabsorbent substances falling into this category are for example modified starch, polymerized polyvinyl alcohol (PVA) and polyethylene oxide (PEO) which are all hydrophilic and have a high affinity to water. When chemically or physically crosslinked, these polymers are water-swellable but not water-soluble. The aforementioned superabsorbent substances have been known for a long time.

In a particular embodiment of the present invention, the superabsorbent substance is a superabsorbent polymer (SAP), in particular in the form of (granular) particles or fibers. In an embodiment, such a SAP is made from polymerization of acrylic acids blended with sodium hydroxide in the presence of an initiated form poly-acrylic acid sodium salt (sometimes referred to a sodium poly-acrylate).

In a further embodiment, the absorbent core containing SAP comprises a carrier layer, wherein the superabsorbent polymer is dispersed in the carrier layer. In an embodiment, the carrier layer in particular may comprise a material selected of a group consisting of tissue paper, a spunlaced polymer, a non-woven fabric, fluff/cellulose, regenerated cellulose as rayon, foam based on different chemistry as polyurethane, alginate, hydrocolloid, carboxymethyl cellulose (CMC) and its derivate and cotton.

In an embodiment, the absorbent core containing SAP comprises at least two carrier layers, which together with the SAP form the absorbent core. For manufacturing, the SAP is dispersed on the first layer, then the second layer is put on top and the two layers are consolidated providing a matrix carrying the SAP between the two layers.

In an embodiment, the absorbent core comprises a carrier layer made of a spunlaced polymer as a non-woven fabric and a granular or fibrous SAP. For manufacturing, the SAP is in a first step, preferably uniformly, dispersed on a first sheet or layer of the spunlaced nonwoven. In a second step, a second sheet or layer of the spunlaced nonwoven is put on top of the first sheet, such that the SAP is located between the two sheets or layers. Then the SAP is integrated in both layers by applying pressure to this sandwich structure provided. By applying pressure, the two layers of spunlaced polymer are consolidated and the SAP to some extent fills up voids in the spunlaced material. The laminate formed this way is soft and looks like a single uniform layer of material.

A non-woven fabric in the sense of the present application is a material made of at least one layer of fibers that have been formed to a web and consolidated in a next step. In particular, consolidation of the non-woven fabric may be achieved by friction and/or cohesion and/or adhesion, for example by needling, felting, spun-lacing, melting or heat embossing.

If compared to tissue paper a material will be considered a non-woven fabric in the sense of the present application once more than 50% of the mass of its fiber components consist of fibers having a ratio of their length to their diameter of more than 300. Alternatively, the material will be considered a non-woven fabric in the sense of the present application if this condition is not fulfilled, but if more than 30% of the mass of its fiber components consist of fibers having a ratio of their length to their diameter of more than 300 and its density is lower than 0.4 g/cm$^3$. This is deemed to be equal to EM 29 092.

While an absorbent core as described above may be advantageous, it is not excluded to design absorbent cores using different material combinations.

An absorbent core, in particular an absorbent core having a superabsorbent substance that in the following text may also be denoted as a superabsorbent core, extracts and stores liquid exudates from a wound, to which the wound dressing is applied to.

In order to avoid direct contact between the absorbent core and the wound surface, the wound dressing further comprises a facing layer.

In order to avoid direct contact between the absorbent core and e.g. a patient's clothing, the wound dressing further comprises a backing layer.

In an embodiment, the facing layer comprises a material selected of a group consisting of a non-woven fabric, e.g. containing polyethylene (PE), polyethylene terephthalate (PET), polypropylene (PP), polyamide or polytetrafluoroethylene (PTFE), a perforated sheet, e.g. containing polyethylene (PE), polyethylene terephthalate (PET), polypropylene (PP), polyamide or polytetrafluoroethylene (PTFE), a perforated sheet laminated on a non-woven fabric, e.g. containing polyethylene (PE), polyethylene terephthalate (PET), polypropylene (PP), polyamide or polytetrafluoroethylene (PTFE), a fine net or screen, e.g. containing polyethylene (PE), polyethylene terephthalate (PET), polypropylene (PP), polyamide or polytetrafluoroethylene (PTFE), a perforated foam or sheet comprising polyurethane, a perforated material based on silicone or a foam with open cells based on polyurethane or silicone or a combination thereof.

In an embodiment, the facing layer comprises a perforated sheet or film, wherein perforations in the facing layer form a three-dimensional structure in order to reduce the sticking surface between the facing layer and the wound surface and to enhance the contact with the wound.

In an embodiment, the facing layer comprises a non-woven fabric consisting of synthetic and/or cellulose fibers. In an embodiment, the fibers of a non-woven fabric forming a facing layer are reoriented such that they predominantly extend in a direction perpendicular to the extension of the facing layer. Such a reorientation of the fibers in the non-woven fabric is achieved by orienting the fibers during the fabrication process, in particular during spun-lacing, needling or electrostatic processing.

In an embodiment of the invention, the facing layer comprises a density in a range from 0.1 g/cm$^3$ to 0.6 g/cm$^3$.

In a further embodiment, the facing layer made of a nonwoven in its unwetted state comprises an area weight (also denoted as the gram weight, basis weight or grammage) in a range from 8 gsm (g/m$^2$) to 50 gsm (g/m$^2$), preferably in a range from 12 gsm (g/m$^2$) to 30 gsm (g/m$^2$).

It is further useful if in an embodiment the facing layer comprises a hydrophobic or hydrophilic surface. This is in particular applicable once the facing layer is brought into direct contact with the wound. Therefore, the facing layer in an embodiment may be coated by non-sticking material, e.g. silicone. In an embodiment, the non-sticking material on the facing layer may be structured to form a pattern with holes on the facing layer.

While it may be that the facing layer is brought into direct contact with the wound (it may then be denoted the contact layer), there may be an embodiment, wherein the wound dressing comprises one or more further layers between the facing layer and the wound. Depending on its functionality in the wound dressing, a person skilled in the art will choose the material of the facing layer in order to fulfil such functionality.

In an embodiment of the present invention, the backing layer serves as a clothing protection. In an embodiment, the backing layer thus is advantageously made of a breathable, non-woven fabric or a breathable film enabling breathing of the wound, but preventing wound exudates from exiting the wound dressing and contaminating a patient's clothing. In a further embodiment the backing layer, in particular when made of a non-woven fabric, is hydrophobic.

In an embodiment of the invention, the backing layer is a hydrophobic nonwoven based on polypropylene with a hydro head in a range from 40 cm H$_2$O to 120 cm H$_2$O, preferably in a range from 50 cm H$_2$O to 80 cm H$_2$O. A backing fulfilling this requirement on the one hand provides a good protection of a patient's clothing while on the other hand avoiding bacteria to enter into the wound dressing. The hydro head in the sense of the present application is the height of a vertical water column standing on and above the surface of the material and which the material can stand against before the water passes through the material to the other side. The numbers given for the hydro head are measured according to ISO 811:1981.

In an embodiment of the invention, the wound dressing comprises a backing layer, e.g. a breathable textile back sheet (BTBS), folded such that it prevents side leakage. An effective prevention of leakage can be achieved by a tubular arrangement, wherein a circumferential portion of the backing layer is folded around the edges of the absorbent core such that it extends at least partially below the absorbent core and overlaps the facing layer. The overlapping portion in direct contact with the facing layer is fixed onto the same, e.g. by gluing. Thereby a leakage of absorbed wound fluid at the side portions of the wound dressing may be effectively prohibited by backing layer, especially a BTBS backing layer.

In an embodiment, the display is mounted on or integrated with a backing layer of the wound dressing. In one embodiment, the display is generated by a printing process. Since the surface structure of the backing layer is in general not suited for a direct printing, the display in one embodiment is printed on a substrate, which in turn is mounted on or integrated with the backing layer. In another embodiment, the backing layer is in a first step prepared by applying a substrate, e.g. a plastic layer, onto the backing layer. In a second step the display is printed onto the prepared substrate on the backing layer. In one embodiment, in a first step a lacquer layer is printed onto the backing layer in order to smoothen the same. Then in a second step a display is printed on the lacquer.

In order improve visibility of the display, the same may be located on an extra area spaced apart from the absorbent core. Thus, even if the portion of the wound dressing with the absorbent core covering the wound is covered by an additional bandage material, like a gauze bandage, the extra area with the display still remains visible.

In an embodiment, the display is mounted on or integrated with a portion of the backing layer extending laterally spaced apart from the absorbent core. Thus, even in case further bandage materials cover the portion of the wound dressing with the absorbent core that covers the wound, e.g. a gauze bandage being warped around, the display on the uncovered portion of the backing layer remains visible. In general, the display may be attached to any suitable surface of the dressing protruding laterally from the wound dressing.

In one embodiment, the display is based on a conducting polymer, preferably on PEDOT:PSS. Poly(3,4-ethylenedioxythiophene) (PEDOT) is used as coloring and counter electrode material in electrochromic displays. The electrically conducting form of PEDOT is obtained by chemical doping of the pristine conjugated polymer, and charge neutrality is then maintained by an excess amount of polystyrene sulfonic acid (PSS), which is a polyanion. Hence, an air-stable and electrically conducting polymer complex PEDOT:PSS is formed. PEDOT:PSS is responsive to electrochemical reduction, wherein not only the color of the material is switched, but also the electronic conductivity. The corresponding color change of the material is utilized in electrochromic displays. An electrochromic display is based on electrochemical reactions on the electrodes. One electrode is reduced and the other is oxidized. Upon changing the oxidation state, the color is changed.

Usage of such a conducting polymer allows for a printable display. This display may be operable at low driving voltages of e.g. a voltage in a range from 1 V to 3 V. The display also has the advantage of being energy efficient, since it only requires an electric current during update or change of the display. To update the display a charge of only 200 nAh/cm$^2$ may be needed. In one embodiment according to the present invention, an updating current is provided to keep the display in a high contrast mode. In an embodiment, the display is further resistant to sterilization methods used for wound dressings, like exposition to ethylene oxide gas.

In an embodiment, the at least one sensor is adapted for determining data on moisture, moisture level, pressure, temperature, and/or pH level.

Corresponding sensors provide an indication of the moisture distribution and level within the wound dressing. Based on these data, the appropriate time for replacement of an almost used up wound dressing as well as status information on the dressing and the wound may be determined. In particular, leakage of the wound dressing can thus be prevented.

In one embodiment, the sensor is adapted to measure the moisture level in the wound bed, wherein the sensor is placed under the facing layer.

Furthermore, data on temperature and pH level of the wound can provide a suitable basis for conclusions on the healing process of the wound. A measurement of the pressure applied to the wound via the dressing and e.g. an additional bandage may be used to judge whether the applied pressure is too large, too small or suitable.

According to an embodiment, the sensor is located (e.g., positioned) between the facing layer and the backing layer, wherein the sensor is preferably located at or integrated with the facing layer, located at or integrated with the backing layer, or located at or integrated with the absorbent core.

A suitable position of the sensor strongly depends on its nature. Temperature and leakage sensors are in some embodiments located at or integrated with the facing layer. A pressure sensor may be either located (e.g., positioned) at or integrated with the facing layer or the backing layer.

A moisture detecting sensor is placed wherever a local occurrence or level of moisture is to be determined. Leakage in general occurs at the facing layer, which results in a need to have a sensor located peripherally between the facing layer and the absorbent core. For detection of saturation, the sensor may instead be placed at the backing layer to sense, when the fluid wets through the absorbent core. To be able to detect pattern of local saturation, there is a need to have sensors spread over larger areas, e.g. in a net or matrix shaped pattern. In one embodiment, moisture sensors are distributed according to a 3D matrix pattern over the wound dressing, thus providing information on the 3D distribution of moisture within the dressing.

Pressure and temperature may be measured based on determining changes in resistance. The moisture may be measured by a potential generated due to the contact between two electrodes of the sensor and an electrolytic wound fluid, i.e. wound exudate.

A measurement of a moisture level is intended to indicate, when it is time to replace a wound dressing. The switching time of the corresponding sensors and display may be set on the order of minutes, since the wetting process of an absorbent core, e.g. with superabsorbent particles, is rather slow, i.e. occurs on similar time scales. The display should be capable to show a corresponding message for about 2 to 7 days, which is the usual period a wound dressing is applied to a wound. It may be beneficial to have an icon, e.g. on the display, that is activated and lights up as soon as the dressing is applied and/or the sensor system/display is activated in order to indicate that the same are working.

In an embodiment of the invention, at least one sensor determines the absolute temperature in order to fulfill the need to indicate and report changes in temperature. In one embodiment, the sensor is adapted for a temperature range of 32° C. to 43° C. For displaying (i.e., presenting) the temperature in both ° C. as well as ° F. a switch device for altering between the values may be provided. Switching time of the sensor and/or display may be on the order of minutes, since the change in temperature is a comparably slow process. In one embodiment, a sensor for determining the temperature is located in the center of the dressing close to the surface of the wound. In one embodiment, a temperature sensor is placed on or under the facing layer in order to determine the temperature of the wound as directly as possible.

A further parameter of interest is the absolute pressure, in particular the pressure generated by applying the dressing onto the wound. Therefore, in an embodiment of the present invention a pressure determining sensor is provided, which is e.g. adapted for a pressure range of 18 mmHg to 70 mmHg with a resolution of 5 mmHg, corresponding to a range of 2.4 kPa to 9.3 kPa with a resolution of 0.7 kPa or a range of 0.4 psi to 1.4 psi. The pressure measured in mmHg may e.g. be visualized in steps of 5 mmHg via the display. This enables simpler drive electronics and a smaller number of display segments. Switching time for sensor and display may beneficially be on the order of seconds, e.g. one second, in order to provide real time information on pressure during fixation of the wound dressing on the wound. In one embodiment, one sensor is located close to the backing of the dressing, i.e. close to, on or under the backing layer.

In order to avoid a need for calibration of each single sensor before applying the wound dressing, use of sensors with only small variations in production is beneficial.

In one embodiment of the present invention, thermistors and thermocouples are used as temperature sensors. Thermistors may be NTC (negative temperature coefficient) as well as PTC (positive temperature coefficient). In order to apply those sensors to the wound dressing preferably printable ink with thermistors may be used, e.g. nano silicon based ink with NTC thermistors. In one embodiment, a printable ink for inkjet printer is used to create a sensitive thermistor. The first layer thereof consists of conductors made of silver and the second layer is made of nickel oxide (NiO) that act as a thermistor due to the semiconducting behavior that changes, when exposed to variations in the temperature. In another embodiment, thermistors are applied that can be surface mounted (SMD) using conducting glue. The thermistor may beneficially be encapsulated in glass for higher accuracy and lower moisture sensitivity.

Different types of pressure sensors may be used for a wound according to the present invention, e.g. piezo resistors, percolations resistors and quantum tunneling composites (QTC). In one embodiment, QTC materials, which change their electrical resistance under pressure, are used in form of an in screen printable ink. QTC materials are based on irregular particles that come close to each other and provide tunneling of electrons between the particles. The materials used to create the particles are e.g. based on Nickel, Copper and Gold. The more particles come close together, the lower the resistance is.

According to an embodiment, the sensor and/or display is arranged on a substrate. In a further embodiment, the sensor and the display are arranged on a common substrate.

In one embodiment, the substrates used for printing on the electronics of the wound dressing are e.g. be PET (polyethylene terephthalate) or PC (polycarbonate). The components are applied, e.g. printed, to the substrate, which afterwards is fixed to the wound dressing. In another embodiment, electronic components are directly printed on the backing layer, wherein a substrate in form of an extra dielectric layer has been deposited prior to printing in order to smoothen the surface for the printed electronics.

In one embodiment, the substrate is cut out as small as possible in order minimize any interference with the properties of the wound dressing.

In one embodiment, the substrate is a plastic layer printed or laminated onto the backing layer in order to create a surface that is compatible with the electronics. This advantageously kept as small as possible in order to keep influence on the properties of the wound dressing down to a minimum. The printed electronics are printed on top of the plastic layer.

To generate a reliable picture showing on the display the moisture level in different areas of the dressing a large number of detection points, i.e. sensors, may be used depending on the accuracy needed, for example 50 measure points per 50 cm$^2$. In one embodiment, the concentration varies locally, e.g. less in the middle and more around the wound to follow the moisture gradient and the status of the wound exuding. Thereby, a picture indicating the status of wound healing or re-epithelialization may be provided on the display.

According to an embodiment, the wound dressing furthermore comprises a microcontroller and/or a data logger and/or an analog to digital to converter and/or a communication interface. The data determined by a sensor according to the present invention, i.e. the signal provided by such a sensor, may be converted from analog to digital by an analog to digital converter. In order to process the data from different sensors and convert the same for a suitable presentation on the display, a microcontroller and a data logger may be used. A communication interface may be used to communicate with external devices and thereby providing access to the data determined by the sensor. An example for such a communication interface is a RFID device.

Examples for suitable chips are the C8051F996 from Silicon Labs, not adapted for wireless communication, or the MLX90129 from Melexis, which can communicate using RFID/NFC. In addition, chips with a battery assisted passive (BAP) configuration, like the RFID sensor chip ANDY100 from Farsens, may be used. Chips adapted for wireless communication may harvest energy from an RF beam emitted by a reader and may additionally comprise an auxiliary battery.

In one embodiment, the microcontroller is mounted using conducting glue and is located outside the dressing next to the display, wherein the microcontroller is mounted on the same substrate as the printed display and/or sensors. In one embodiment, also a data logger and/or an antenna are mounted in an analogous way. Further electronic devices like data logger, analog to digital converter or communication interface may be mounted similarly.

According to one embodiment, the wound dressing comprises a chip, i.e. microcontroller, adapted for wireless communication together with a corresponding antenna. Chips adapted for wireless communication with a wireless device, e.g. a smart phone, do not require a battery in the wound dressing, due to power transmittance through an antenna. In combination with a suitable antenna design energy is harvested e.g. from the NFC. A wireless communication offers the additional possibility of easily visualizing the result on exterior displays.

According to another embodiment, the wound dressing furthermore comprises a battery. For systems including a battery, chips may be used that cannot communicate wirelessly.

In an embodiment, the battery is a galvanic cell formed by the sensor, wherein the sensor comprises two electrodes, i.e. an anode and a cathode, which are adapted to be activated by a wound fluid. Wound fluid in general consist to 0.9% of NaCl and is therefore suitable as an electrolytic fluid for a galvanic element.

A galvanic element in terms of the present invention is every combination of at least two different electrodes and an electrolyte.

In an embodiment of the invention, the battery is a passive battery, e.g. in form of a galvanic element, which is activated by the wound fluid acting as an electrolyte. The battery as provided by the wound dressing does not comprise any electrolyte per se. Thus, in order to generate voltage, the electrodes have to be exposed to the wound fluid acting as an electrolyte.

In one embodiment of the present invention, a passive battery is formed by a sensor comprising two different electrodes. The sensor in turn provides a voltage to drive a change of the display. Thus, the display is updated by the sensor to indicate that it is time to change the dressing, when wound fluid connects the two electrodes of the battery generating a potential and a corresponding voltage signal is transferred to the display.

Three factors define the capability of a sensor to function as a battery, which are the electrode materials, capacity and the internal resistance. The choice of the electrode material determines the theoretical voltage that can be generated. The internal resistance influences the practical output voltage generated from the sensor. The capacity is determined by the amount of active material used in the electrode, which needs to contain enough charge carriers to update the display.

According to one embodiment of the invention, the sensor is printed by using a mixture of ink with metal oxides, wherein for cathode and anode different types of oxides are used.

Materials for the anode may be zinc provided as a coating on carbon or zinc blended with carbon at different ratios and for the cathode $MnO_2$ blended with carbon at different ratios or $Ag_2O$ blended with carbon at different ratios.

In one embodiment, a material combination for the electrodes is zinc in combination with PEDOT:PSS. The zinc particles are mixed with carbon in order to obtain a uniform conductivity in the electrode. Furthermore, zinc and silver oxide are used as electrode materials. The silver oxide may preferably be divalent (AgO) or monovalent ($Ag_2O$) silver oxide. The conductivity of the monovalent silver oxide is however rather poor. To increase the conductivity of the silver oxide, it may be mixed with carbon powder. Since for an application according to the present invention with a low energy display no powerful battery is needed, the carbon may instead be mixed with silver oxide.

In another embodiment, $Zn/MnO_2$ electrodes are used, wherein the $MnO_2$ is e.g. blended with carbon to achieve a higher conductivity. In yet another embodiment, a Fe/AgO combination is used, providing high reliability, long life and better durability. Iron and silver oxide are mixed in a carbon ink to achieve functionalized electrodes.

Furthermore, in one embodiment a bio fuel cell is used, which is triggered by the wound fluid. This technology is based on enzyme reactions or bacteria that mimics the interactions found in nature.

In one embodiment, an autonomous battery is provided. It is advantageous to use an all-printed power source, which is thin and flexible, e.g. based on zinc and manganese dioxide with zinc chloride as an electrolyte.

Even in case of embodiments comprising an autonomous battery or antenna as power sources, for the moisture sensor a similar sensor design may be used as for the battery-like sensor concept. In those embodiments, the sensor does not need to generate a certain potential. It is sufficient to measure the change in impedance as the absorbent core is absorbing moisture, wherein an increasing amount of moisture will result in a decrease in impedance. The electrodes in the sensors may be based on silver, carbon, or conducting polymers, which may be patterned using common printing technologies.

In an embodiment, the electrodes are flat and have a preferably circular, elliptical, rectangular or square shape. In another embodiment, the electrodes are elongated and form closed loops with a preferably circular, elliptical, rectangular or square shape.

According to an embodiment, the wound dressing comprises two or more sensors.

Taking into account the general propagation path of the wound fluid in the wound dressing, sensors may be formed and placed such that they are exposed to moisture, when a certain level of saturation is reached. Alternatively or additionally, a sensor may be placed such that the fluid has to come in contact with the same, when the fluid is going to leak out of the wound dressing.

According to an embodiment, the wound dressing comprises at least two sensors, the electrodes of which are arranged concentrically within in a common plane and/or on parallel planes. The sensors will trigger as soon as the liquid reaches a portion of the same. Thus, activation of the sensors one after another provides information on the dynamical progress of the fluid within the wound dressing.

In an embodiment comprising at least two sensors, the electrodes are elongated, straight and extend parallel to each other within in a common plane and/or on parallel planes.

In an embodiment, a plurality of sensors are positioned according to a two-dimensional (2D) and/or a three-dimensional (3D) matrix. Based on the data gained by those sensor are 2D or 3D pictures of the moisture distribution and its progress within the wound dressing may be provided on the display. According to one embodiment, the absorbent core is formed by at least three absorbent sub-layers, wherein at least two sensors are arranged between different sub-layers. Thereby a complex 3D distribution of sensors within the dressing is implemented.

The above object is also solved by a method for manufacturing a wound dressing comprising the steps of printing a display, which is adapted to receive data determined by at least one sensor in form of an electrical signal and to display the received data, onto the wound dressing and providing the at least one sensor.

The wound dressing may be provided according a known methods for manufacturing. In an embodiment, the wound dressing is prepared by applying a substrate onto the same and the display is printed onto the prepared substrate.

One embodiment of a method for manufacturing a wound dressing according to the present invention comprises the steps of providing an absorbent core, providing a facing layer, providing a backing layer, and locating the absorbent core between the facing layer and the backing layer, preparing the backing layer by applying a substrate onto the backing layer, printing a display, which is adapted to receive data determined by at least one sensor in form of an electrical signal and to display the received data, onto the prepared substrate and providing the at least one sensor.

Providing the sensor may include locating the same at or integrated with the facing layer, the backing layer or the absorbent core. According to one embodiment, the backing layer is prepared and the display is printed before the absorbent core is located between the facing layer and the backing layer. In one embodiment, the sensor is printed on the same substrate as the display. According to an embodiment of the invention, a further substrate is applied to the backing layer or the facing layer and the sensor is printed onto the further substrate. In one embodiment, the absorbent core provided is formed by sub-layers, wherein at least one sub-layer is prepared by applying a substrate to the sub-layer and the sensor is printed onto the prepared substrate.

As far as aspects of the present invention have been described above regarding the wound dressing, they also apply to a process for manufacturing such wound dressing and vice versa.

Further advantages, features and applications of the present invention will become apparent from the following description of embodiments and the corresponding figures attached.

Figure 2:
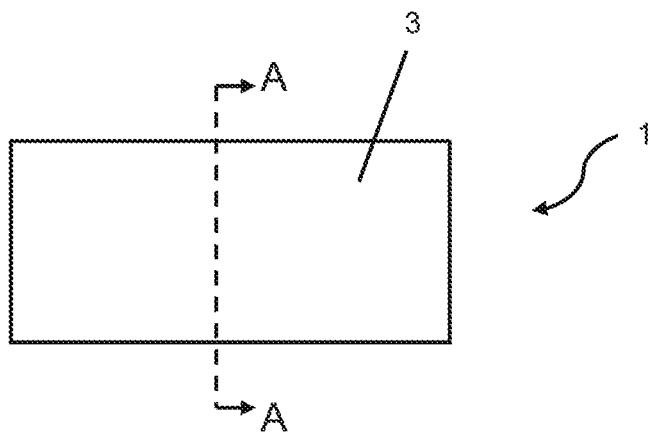
FIG. 2 shows a schematic top view onto the wound dressing of FIG. 1 from a facing side.

According to FIGS. 1 and 2, a first embodiment of a wound dressing 1 comprising features of the invention is schematically depicted.

FIG. 1 shows a schematic top view of the top side of a wound dressing 1 according to the present invention. The top surface is formed by a backing layer 4 with a display 8 mounted thereon. In FIG. 2 the opposite surface, i.e. the bottom surface, of the wound dressing 1 of FIG. 1 is shown. The bottom surface is formed a facing layer 3.

Figure 3:
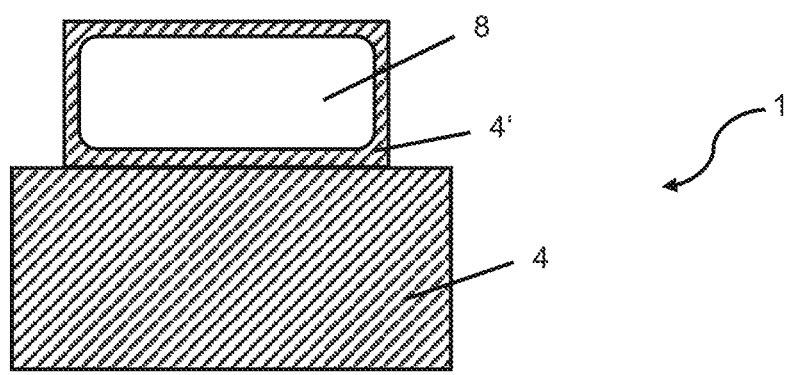
FIG. 3 shows a schematic top view onto the backing side of a wound dressing with a laterally displaced display according to a second embodiment of the present invention.

In FIG. 3 an alternative embodiment of a wound dressing 1 according to the present invention is shown, wherein the display 8 is mounted on or integrated within the top side of a portion 4' of the backing layer extending laterally spaced apart from the absorbent core 2 of the dressing 1. The portion 4' shown in FIG. 3 is arranged along a long side of the rectangular backing layer 4. In an alternative embodiment, portion 4' may be positioned along any other side of backing layer 4. When a wound dressing is additionally wrapped with further dressing material like a gauze bandage a display mounted on the backing layer 4 according to FIG. 1 may be covered by the same. Thus, a display 8 located on an extra portion of the backing layer 4 remains visible, even if the portion of the wound dressing 1 covering the wound is wrapped. The display may be placed on the top or the bottom side of the portion 4'. Located on the bottom side, the same may be folded around such that the top side rests on the gauze bandage, where it may be additionally fixed. Thus, the display 8 will be easily visible on top of the gauze bandage. In general, the display 8 may be placed on any arbitrary kind of substrate attached to the wound dressing 1 and laterally projecting from the same, such that the display 8 remains visible even if the rest of the wound dressing 1 is covered by additional dressing material.

The wound dressing 1 consists of a layered structure which is best understood when considered with reference to the cross-sectional drawings of FIGS. 4A, 4B and 4C, showing three alternative embodiments of the layered structures comprised by the wound dressing shown in FIGS. 1 and 2.

The wound dressing 1 of FIG. 4A comprises an absorbent core 2, which in this particular embodiment has two sub-layers 2a, 2b made of tissue paper with a superabsorbent polymer in the form of granular particles dispersed between the two sub-layers 2a, 2b. The two sub-layers together form the carrier layer of the absorbent core. In order to manufacture the absorbent core 2 the superabsorbent particles are dispersed on a first sub-layer 2b thereof and then the second sub-layer 2a is consolidated on top of the first sub-layer 2b providing a fixation of the superabsorbent particles.

In order not to come into direct contact with the wound on the one side and e.g. a clothing of the patient on the other side, the absorbent core 2 is wrapped or enveloped in a pouch formed by a facing layer 3 and a backing layer 4.

The facing layer 3 in this particular embodiment is made of a white hydrophilic non-woven fabric consisting of polypropylene fibers in order to provide a good transport of exudate from a wound to the absorbent core 2.

As an example, the backing layer 4 serves as a clothing protection and is made of a green breathable, hydrophobic non-woven fabric based on polypropylene. The non-woven has a hydro head of 50 cm/$H_2O$. This backing layer 4 allows breathing of the wound while simultaneously preventing wound exudates from exiting the wound dressing and contaminating a patient's clothing.

Under the backing layer 4 a moisture determining sensor 5 is placed. This sensor 5 is in contact with the absorbent core 2. When wound fluid is absorbed and the absorbent core 2 reaches its saturation limit such that its top surface becomes wet and fluid may exit, the sensor 5 provides a corresponding voltage signal to the display 8. The display 8 is updated and indicates that it is time to replace the wound dressing 1 before it is completely saturated such that no further wound fluid is absorbed and the healing process may be negatively influenced.

In FIG. 4A the facing layer 3 and the backing layer 4 have been joint together by two seams 18, 19 extending above the absorbent core. In order to do so, the facing layer 3 has been folded in parallel to its long edges such that it also extends above the absorbent core 2 and it partly covers the top surface of the absorbent core 2. Furthermore, the facing layer 3 entirely covers the bottom surface of the absorbent core 2.

A location of the seams in an area above the absorbent core 2, i.e. in a position where the facing layer 3 and the backing layer 4 overlap above the absorbent core 2, has the advantage that no reddening due to stiff edges along the long side of the wound dressing 1 occur. When considered in a cross-section along the line A-A of FIG. 2 the wound dressing 1 thus has a tubular structure as shown in FIG. 4A.

Different designs of sensors 5, e.g. moisture sensors, may be used in combination with each other. Furthermore, in one embodiment with an absorbent core 2 comprising at least two core layers 2a, 2b, the sensors 5 may be placed between both layers 2a, 2b. In embodiments with more than two core layers, the sensors 5 may be placed between different core layers, i.e. on different levels in the wound dressing 1. Sensors 5 distributed in three dimension over the wound dressing 1, e.g. between different core layers, allow to gain and display information on the development of the saturation status and the moisture distribution in 3D.

In addition, a wound moisture level detection sensor 5 may be provided detecting the moisture degree in different areas of the wound dressing corresponding to different areas of the wound as well as around the same. The moisture level may be determined by impedance measurements and e.g. translated into microgram/$cm^2$ or similar. By using an advanced sensor system with an adequate chip solution, both leakage and saturation degree as well as moisture level in the wound may be displayed (i.e., presented).

In FIG. 4B an embodiment of the wound dressing 1' with an alternative arrangement of the layered structure is shown.

The cross-sectional view along a line corresponding to the line A-A of FIG. 2 again illustrates a tubular structure. However, in this alternative embodiment the backing layer 4 has been folded in parallel to its long edges such that it extends beneath the absorbent core 2 and partly covers the bottom surface of the absorbent core 2. Furthermore, the backing layer 4 entirely covers the top surface of the absorbent core 2.

As the embodiment of FIG. 4A, the embodiment of FIG. 4B avoids reddening due to stiff edges along the long side of the wound dressing 1' occur. Furthermore, the tubular structure of the breathable, hydrophobic backing layer 4, preferably made of a BTBS material, effectively minimizes the risk of a lateral leakage of wound fluid.

FIG. 4C shows a standard arrangement for the connection of backing layer 4 and facing layer 3 attached to each other via overlapping seams 18, 19 extending circumferentially around the absorbent core 2. The present invention may be advantageously applied even to those standard wound dressings 1".

FIG. 4D shows an arrangement in which the absorbent core 2 is formed by at least three absorbent sub-layers 2a, 2b, 2c.

FIG. 4E shows an arrangement in which the sensor 5 is arranged on a substrate of a plastic layer 22 and the substrate is laminated onto an exterior surface of the backing layer 4.

FIG. 4F shows an arrangement in which the sensor 5 is arranged on a substrate of a plastic layer 22 and the substrate is laminated onto a surface of the backing layer 4 facing the absorbent core 2.

FIG. 4G shows an arrangement in which the sensor 5 is arranged on a substrate of a plastic layer 22 and the substrate is laminated onto an exterior surface of the backing layer 4, wherein the sensor 5 is arranged between the exterior surface of the backing layer 4 carrying the substrate and the substrate.

FIG. 4H shows an arrangement in which the sensor 5 is arranged on a substrate of a plastic layer 22 and the substrate is laminated onto a surface of the facing layer 3.

FIG. 5 shows an embodiment of the invention with a single sensor 5 adapted as a leakage sensor located under the facing layer. The sensor 5 is electrically conductive interconnected with a display 8. This sensor 5 may e.g. be applied to any wound dressing of FIGS. 4A to 4C. The backing layer 4 consist of a hydrophobic sandwich material, while the facing layer 3 is made of a hydrophilic sandwich material. To reduce the risk of leakage from the start, a BTBS back facing 4 with a reversed tube design as shown in FIG. 4B may be used. The sensor 5 comprises an anode 15 and a cathode 16 extending parallel to each other around the edges of an imaginary rectangle. The electrodes 15, 16 comprise a line structure, which extends parallel and spaced apart from the edge of the wound dressing 1. In one embodiment, it may be placed about 10 to 30 mm from the edge, in one embodiment the electrodes may be placed up to 50 mm from the edge. When the wound fluid spreads within the wound dressing, it will ultimately reach the two electrodes 15, 16 of the sensor 5 and establish an electric contact between them. Thus, the galvanic element constituted by the anode 15, the cathode 16 and the electrolytic wound fluid will be activated and a corresponding potential is generated. The resulting voltage signal will update the display 8. The display 8 may show a percentage value of the saturation degree of the dressing 1, depending on the position and size of the sensor 5 e.g. 70%, 80%, 90% or up to 100%. The larger the closed loop formed by the sensor 5 is, the larger the saturation level of the wound dressing 1, which has to be reached such that wound fluid comes into contact with electrodes 15, 16. The sensor 5 is preferably arranged such that the display 8 indicates a saturation degree sufficiently below 100% to indicate in time that it is time to change the dressing 1.

The embodiment, schematically shown in FIG. 6, corresponds to the one according to FIG. 5 except for the fact that in FIG. 6 two concentrically arranged sensors 5 and 6 are provided. Both sensors 5 and 6 are adapted for moisture determination and designed as galvanic elements to be activated by wound fluid. The first, inner sensor 6 may be located spaced apart from the edge of the wound dressing 1 such that the enclosed area corresponds to about 30% to 60% of the absorbent core area, while the second, outer sensor 5 may enclose about 70% to almost 100% of the absorbent core area. Thus, when wound fluid exits the core 2 and reaches the backing layer 4, the inner sensor 6 will in general be activated first, giving a progress report of the saturation status of the dressing 1. When the wound fluid spread, the outer sensor 5 will ultimately be activated, indicating that the dressing 1 has to be replaced soon. The result of the two sensors 5, 6 may be displayed (i.e., presented) in the same segment of the display 8. They may alternatively be displayed in different segments of the display 8 or there may be provided more than one display 8, thus displaying every result on a different display 8. Compared to the embodiment according to FIG. 5, the embodiment of FIG. 6 provides more information regarding need for change of the dressing 1, in particular about the progress of saturation. Furthermore, it may allow for a better understanding, when maceration starts.

FIG. 7 is a schematic diagram of a sensor arrangement according to the present invention with four identical straight strip-like sensors 5 arranged parallel to each other. Those sensors may be placed on or under the backing layer 4 of a wound dressing 1. There may be more or less stripes provided depending on necessity, e.g. 4 to 10 stripes. Each stripe comprises an anode 15 and a cathode 16, extending parallel too each other. Arranged at the backing layer 4 of the dressing 1, those sensor stripes are provided for detecting a strike through of wound fluid, especially if the backing layer 4 comprises hydrophilic materials. When the fluid has spread upwards through the dressing 1 and reaches the backing layer 4, each single sensor 5 will send a signal to the display 8 as soon as it is activated by contact with the electrolytic wound fluid. In one embodiment, the display 8 provides a light for every sensor 5. In another embodiment, the display 8 comprises no light sources, but is based on a change of contrast, e.g. the color changes from a light blue to a deep blue. In such an embodiment, the display 8 may provide a color changing segment for each sensor 5. Thus, the lights in the display 8 will be turned on one by one, when the fluid strikes through, indicating an immediate need for replacement of the dressing 1. This sensor arrangement provides for a better understanding, when the dressing is filled up and when maceration starts.

In an embodiment of the present invention, the sensor arrangements as shown in FIGS. 5, 6, and 7 may also be combined with each other.

In FIG. 8A, an embodiment of a combined saturation and leakage sensor 5 based on a net-like structure is shown. The net 22 may comprise a plurality of single sensors 5 arranged at the knots of the net 22. Alternatively, the net structure may be formed by a single sensor 5, i.e. every thread of the net is formed by a stripe comprising two electrodes 15, 16. Considering the net 22 as a matrix structure, from knowing which columns and which rows have been activated, it may be derived, where the wound fluid spreads over the net area.

This embodiment is based on a chip solution with an active battery (not shown), wherein the sensor(s) 5 measure local impedances. The mesh size may be adapted as needed. The chip receives those signals on impedance and converts the same to the display 8. The net 22 may be placed above or below a portion of or the complete backing layer 4 and/or above or below a portion of or the complete facing layer 3. The covered area may e.g. reach from about 40% up to 90% of the backing layer 4 and/or facing layer 3. A smaller area covered by the net 22 requires a smaller battery capacity and thus allows for cheaper solution, while a larger area gives a more complete picture of the dressing status. This sensor 5 may show a real time picture of the saturation degree in the dressing 1, which helps the nursing staff to understand what is happening in the wound due to maceration and to judge when it is time to replace the dressing 1. The results may be displayed on a display 8 as an e.g. color coded picture of the real time distribution of the saturation degree over the complete net area or as a percentage (%) value for the complete net 22. Furthermore, the sensor 5 may detect the moisture level in different areas of the wound and around the wound. This information, when displayed by the display 8, may help a specialist nurse to understand the moisture status in the wound.

Figure 8B:
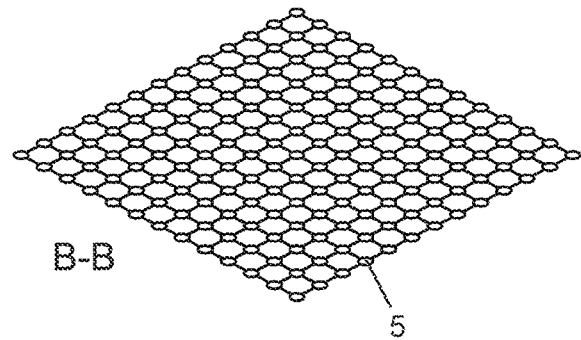
FIG. 8B shows schematic cross-sectional view along line B-B of FIG. 8A and depicts a plurality of sensors mounted to, or integrated with, the wound dressing according to a two-dimensional matrix.
Figure 8C:
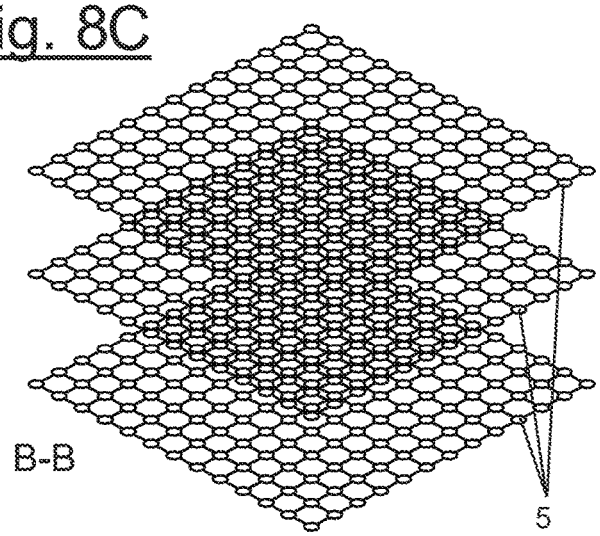
FIG. 8C shows schematic cross-sectional view along line B-B of FIG. 8A and depicts a plurality of sensors mounted to, or integrated with, the wound dressing according to a three-dimensional matrix.

FIGS. 8B and 8C show schematic cross-sectional views along line B-B of FIG. 8A. FIG. 8B depicts a plurality of sensors 5 mounted to, or integrated with, the wound dressing according to a two-dimensional matrix. FIG. 8c depicts a plurality of sensors 5 mounted to, or integrated with, the wound dressing according to a three-dimensional matrix.

Figure 9A:
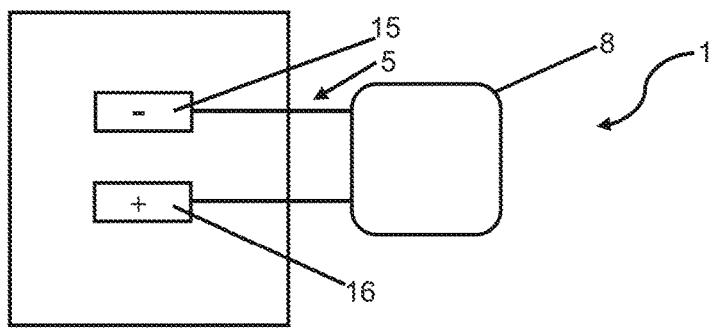
FIGS. 9A and 9B illustrate a moisture determination procedure based on a single sensor with two flat, rectangular electrodes.
Figure 9B:
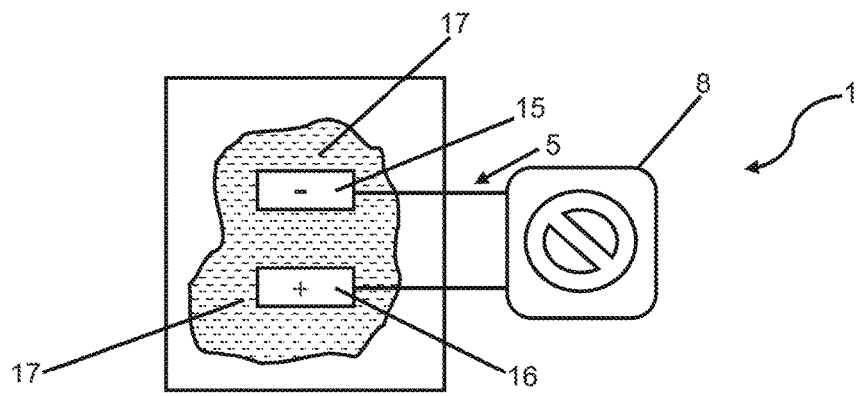

FIGS. 9A and 9B illustrate the method of detecting moisture via a sensor 5 formed as a galvanic element. In FIG. 9A a single sensor 5 comprising an anode 15 and a cathode 16 is shown, both electrodes in the form of flat rectangular elements. Without any electrolytic fluid establishing an electrically conductive interconnection between the two electrodes 15, 16, the display 8 indicates nothing. When wound fluid 17 spreads between the anode 15 and cathode 16, an electrical contact is established and based on the resulting potential a voltage signal is transferred to the display 8. Thereby, the display 8 is updated and indicates that a certain saturation level has been reached. The display may e.g. indicate that the dressing 1 is almost entirely saturated and must be replaced soon.

Figure 10A:
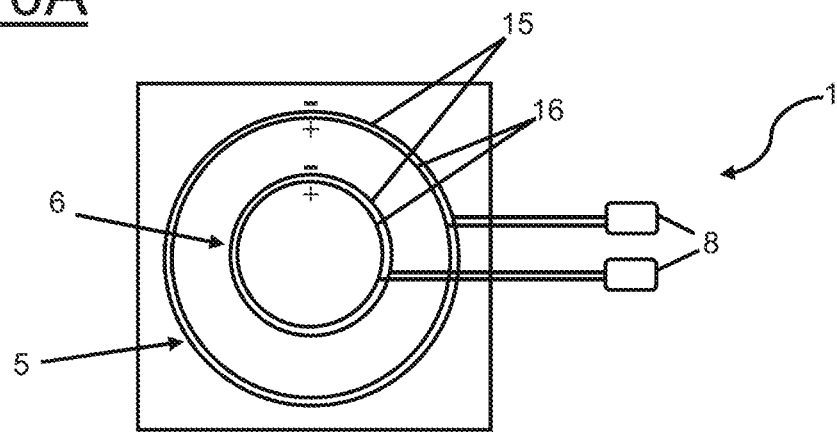
FIGS. 10A to 10C illustrate a moisture determination procedure based on two concentrically arranged circular sensors.
Figure 10B:
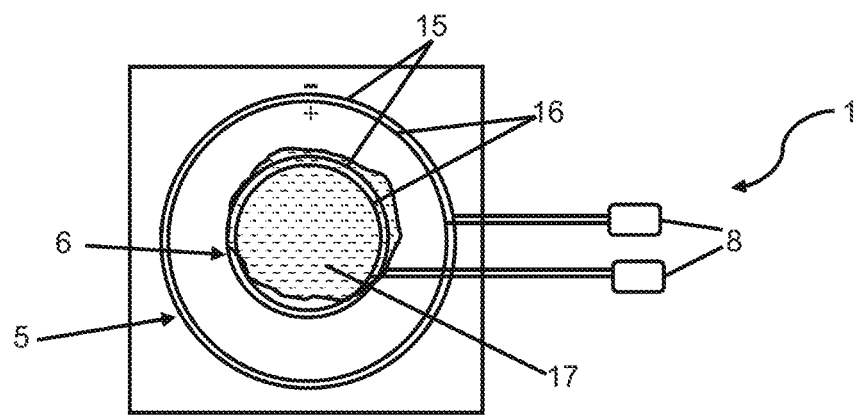
Figure 10C:
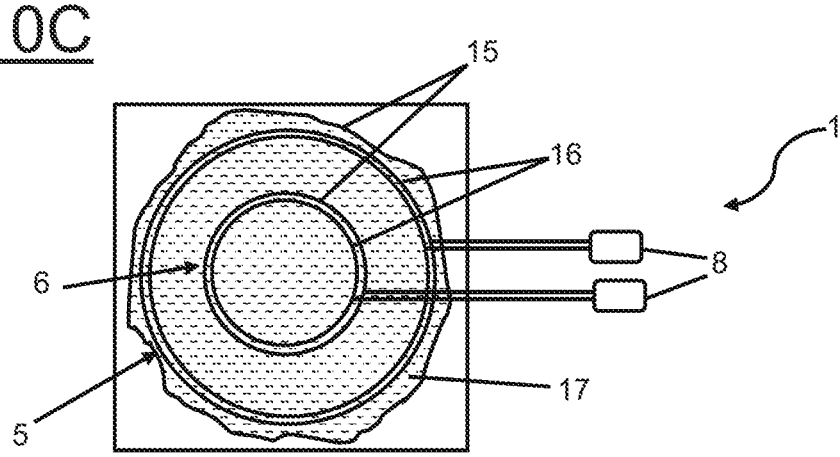

In FIGS. 10A to 10B, a detection and determination method for a sensor arrangement corresponding to the one shown in FIG. 6 is illustrated. A schematic diagram of two concentrically aligned circular shaped sensors 5, 6 is shown, wherein the fluid may enter in the middle and then diffuse laterally towards the sensors 5, 6. The sensors 5, 6 are formed as galvanic elements. As long as no electrolytic fluid has reached any of the electrodes 15, 16, no signal is transferred to the display 8. Again, signals of the two sensors 5, 6 may be displayed (i.e., presented) in the same segment of a display, in different segments of the same or even on different displays. As soon as wound fluid 17 has reached the first sensor 6, the corresponding galvanic element is activated and on display 8 an information, e.g. a percentage (%) value, is shown indication the saturation level corresponding to the first sensor 6. Thus, exposure of the inner rings to the fluid 17 may result in triggering a first level note of "50%" on display 8. When more fluid 17 is absorbed and the same spreads further, it comes in contact with the second senor 5, resulting in a second information displayed on display 8, e.g. a percentage (%) value of the saturation level corresponding to the second sensor 5. For example, "100%" may be shown on the display 8, indicating an immediate need for replacing the wound dressing 1. The second information may be shown in addition to the first one or replace the first one. Thereby, information on the moisture distribution over time is provided.

Figure 11A:
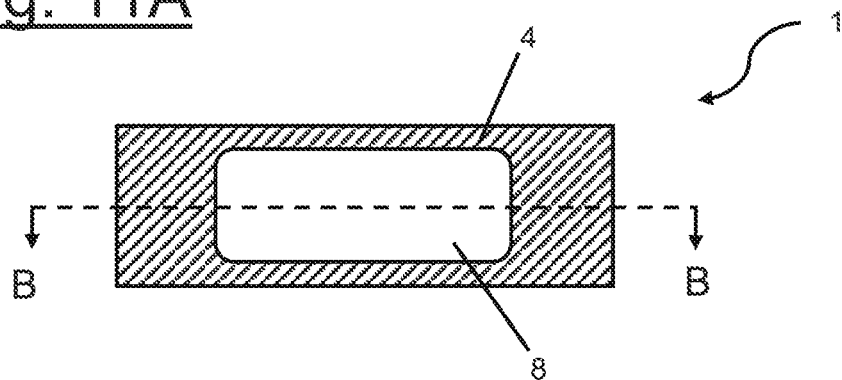
FIGS. 11A and 11B show a schematic top view of an adhesive bandage and a schematic cross-sectional view along line B-B of FIG. 11A, respectively.
Figure 11B:
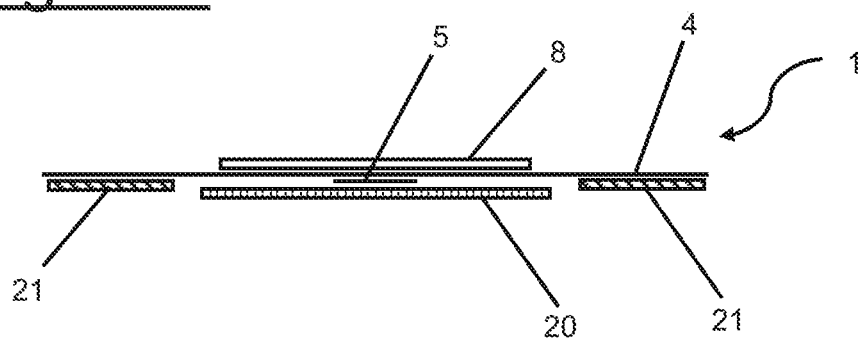

In FIGS. 11A and 11B a wound dressing 11 in form of an adhesive bandage or plaster is shown. FIG. 11A shows a schematic top view of the top side of an adhesive bandage 1 according to the present invention. The top surface is formed by a backing layer 4 with a display 8 mounted thereon. The adhesive bandage 1 of FIG. 11B, which shows a schematic cross-sectional view along line B-B of FIG. 11A, comprises a backing layer 4. On the backing layer 4 a display 8 is mounted, under the backing layer 4 an absorbent pad 20 is located. The bottom side of the backing layer 4, which laterally extends beyond the absorbent pad 20, is provided with a self-adhesive film 21. These sections of the backing layer 4 with the adhesive film 21 are intended to be attached to a patient's skin, while the backing layer 4 prevents direct contact between the absorbent pad 20 and a patient's clothing. A sensor 5 is located between the backing layer 4 and the absorbent pad 20. The sensor 5 is e.g. a moisture determining sensor. This sensor 5 is in contact with the absorbent pad 20 and provides a corresponding voltage signal to the display 8, when fluid leaks from the absorbent pad 20. The display 8 is updated and indicates that it is time to replace the adhesive bandage 1.

Figure 12:
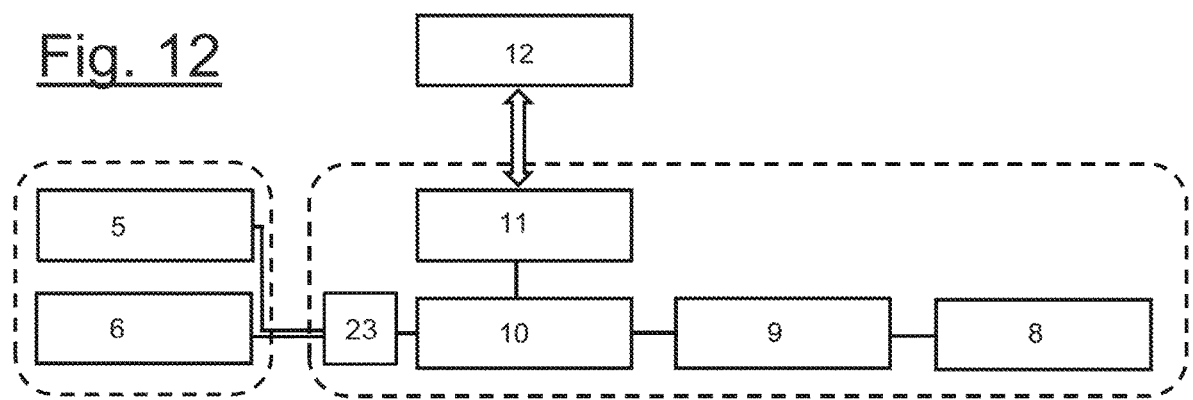
FIG. 12 shows a schematic diagram of a circuit with a microcontroller using an external reader and an antenna as energy source.

FIG. 12 shows a diagram of a circuit comprising a chip, i.e. microcontroller 9, which wirelessly communicates with and harvests energy from an external reader 12, e.g. a RF reader, when it is time for a measurement. Therefore, an antenna 11 is provided for communication between the external reader 12 and the microcontroller 9 via a data logger 10. There may also be analog to digital converter 23 provided for converting analog sensor signals to digital data. There are two sensors 5 and 6 provided within a wound dressing 1, e.g. a pressure and a temperature sensor, providing information on the temperature and applied pressure via date logger 10 and microcontroller 9 to the display 8. A moisture sensor may alternatively or additionally be provided at the same location as sensors 5 and 6 within the circuit. Besides being communicated with the patient by the display 8 of the wound dressing 1 the result can additionally be displayed (i.e., presented) on an external reader 12 such as a smart phone. With a chip 9 harvesting energy from the external reader 12, there is no need for a battery, which lowers the costs and simplifies recycling of the final product.

Figure 13:
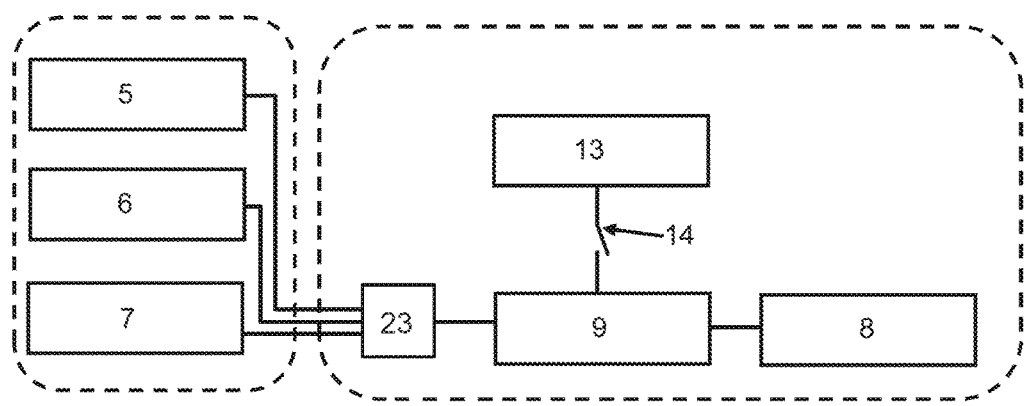
FIG. 13 shows a schematic diagram of a circuit with a microcontroller using an autonomous battery as energy source.

FIG. 13 shows an alternative embodiment of a circuit according to the present invention. The circuit of FIG. 13 uses a printed battery 13 as an energy source for power supply. The microcontroller 9 performs the measurements on the sensors 5, 6, 7 and displays the result on the display 8. There may also be analog to digital converter 23 provided for converting analog sensor signals to digital data. This circuit provides a triggering function via switch 14 in order ensure for the battery 13 to last the shelf time needed. A time triggering function may be implemented by starting the circuit when the wound dressing 1 is mounted and then showing the results at specific times/time intervals or the result is displayed, when activated via an additional activation means like a push button. In the embodiment according to FIG. 13, three sensors 5, 6, 7 are provided, which are e.g. a pressure, a temperature as well as a moisture sensor.

For purposes of original disclosure it is pointed out that all features which are apparent for a person skilled in the art from the present description, the figures and the claims, even if they have only been described with further features, could be combined on their own or together with all the combinations of the features disclosed herein, if not excluded explicitly or technically impossible. A comprehensive explicit description of all possible combinations of features is only omitted in order to provide readability of the description.

In the figures identical elements have been denoted by identical reference numbers. The figures only represent schematic views and are not to scale.

What is claimed is:

1. A wound dressing comprising:
an absorbent core;
a facing layer;
a backing layer made of a breathable non-woven fabric or a breathable film, wherein the absorbent core is located between the facing layer and the backing layer;
at least one sensor generating a sensor signal, wherein the sensor is arranged on a substrate of a plastic layer and the substrate is laminated onto an exterior surface of the backing layer; and
a display configured to receive the sensor signal from the at least one sensor and present data corresponding to the sensor signal, wherein the display is mounted to or integral with the wound dressing.

2. The wound dressing of claim 1, wherein:
the at least one sensor comprises a plurality of sensors;
the absorbent core is formed by at least three absorbent sub-layers; and
at least two of the plurality of sensors are located between different sub-layers.

3. The wound dressing of claim 1, wherein the display is mounted to or integrated with the backing layer of the wound dressing.

4. The wound dressing of claim 3, wherein the display is mounted to or integrated with a portion of the backing layer extending laterally spaced apart from the absorbent core.

5. The wound dressing of claim 1, wherein the at least one sensor is configured to generate data pertaining to at least one parameter selected from a group consisting of a moisture, a moisture level, a pressure, a temperature, and a pH level.

6. The wound dressing of claim 1, wherein the display is disposed on the substrate of the plastic layer on which the sensor is arranged.

7. The wound dressing of claim 1, further comprising:
a microcontroller, a data logger, an analog digital converter, or a communication interface.

8. The wound dressing of claim 1, further comprising:
a battery.

9. The wound dressing of claim 1, wherein:
the at least one sensor forms a galvanic cell battery; and
the at least one sensor comprises at least two electrodes that are configured to be activated by a wound fluid.

10. The wound dressing of claim 9, wherein:
the electrodes are elongated and form a closed loop with a circular, elliptical, rectangular or square shape.

11. The wound dressing of claim 1, wherein:
the at least one sensor comprises a plurality of sensors mounted to, or integrated with, the wound dressing according to a three-dimensional matrix.

12. A method for manufacturing the wound dressing of claim 1, comprising:
printing, onto the wound dressing, a display, the display configured to receive at least one sensor signal generated by at least one sensor and the display configured to present data corresponding to the sensor signal; and
mounting to, or integrating with, the wound dressing the at least one sensor.

13. The method of claim 12, further comprising:
locating an absorbent core between a facing layer and a backing layer; and
applying a substrate onto the backing layer;
wherein printing, onto the wound dressing, the display comprises printing the display onto the substrate applied onto the backing layer.

14. The method of claim 13, further comprising:
locating the at least one sensor between the facing layer and the backing layer, wherein the at least one sensor is located at, or integrated with, the absorbent core.

15. The method of claim 13, wherein:
the at least one sensor comprises a plurality of sensors;
the absorbent core is formed by at least three absorbent sub-layers; and
at least two of the plurality of sensors are located between different sub-layers.

16. The method of claim 12, further comprising:
mounting to, or integrating with, the wound dressing a microcontroller, a data logger, an analog digital converter, or a communication interface.

17. The method of claim 12, further comprising:
mounting to, or integrating with, the wound dressing a battery.

18. The method of claim 12, wherein:
the at least one sensor forms a galvanic cell battery; and
the at least one sensor comprises at least two electrodes that are configured to be activated by a wound fluid.

19. A wound dressing comprising:
an absorbent core;
a facing layer;
a backing layer made of a breathable non-woven fabric or a breathable film, wherein the absorbent core is located between the facing layer and the backing layer;
at least one sensor generating a sensor signal, wherein the sensor is arranged on a substrate of a plastic layer and the substrate is laminated onto a surface of the backing layer facing the absorbent core; and
a display configured to receive the sensor signal from the at least one sensor and present data corresponding to the sensor signal.

20. A wound dressing comprising:
an absorbent core;
a facing layer;
a backing layer made of a breathable non-woven fabric or a breathable film, wherein the absorbent core is located between the facing layer and the backing layer;
at least one sensor generating a sensor signal, wherein the sensor is arranged on a substrate of a plastic layer and the substrate is laminated onto an exterior surface of the backing layer, wherein the sensor is arranged between the exterior surface of the backing layer carrying the substrate and the substrate; and
a display configured to receive the sensor signal from the at least one sensor and present data corresponding to the sensor signal, wherein the display is mounted to or integral with to the wound dressing.

21. A wound dressing comprising:
an absorbent core;
a facing layer;
a backing layer made of a breathable non-woven fabric or a breathable film, wherein the absorbent core is located between the facing layer and the backing layer;
at least one sensor generating a sensor signal, wherein the sensor is arranged on a substrate of a plastic layer and the substrate is laminated onto a surface of the facing layer; and a display configured to receive the sensor signal from the at least one sensor and present data corresponding to the sensor signal, wherein the display is mounted to or integral with the wound dressing.

\* \* \* \* \*